(12) United States Patent
Lorant et al.

(10) Patent No.: US 6,623,769 B1
(45) Date of Patent: Sep. 23, 2003

(54) ADMINISTRATION OF LYCOPENE FOR COMBATING SKIN/MUCOUS MEMBRANE DAMAGE

(75) Inventors: Raluca Lorant, Thiais (FR); Lionel Breton, Versailles (FR); Christel Liviero, Paris (FR)

(73) Assignee: Societe L'Oreal S.A., Paris (FR)

( * ) Notice: Subject to any disclaimer, the term of this patent is extended or adjusted under 35 U.S.C. 154(b) by 0 days.

(21) Appl. No.: 09/684,984

(22) Filed: Oct. 10, 2000

(30) Foreign Application Priority Data

Oct. 7, 1999 (FR) ............................................. 99 12507
Mar. 27, 2000 (FR) ............................................. 00 03849

(51) Int. Cl.$^7$ ............................................. A61K 35/78
(52) U.S. Cl. ...................... 424/777; 424/725; 514/456; 514/458; 514/725; 514/764; 514/886
(58) Field of Search ................................ 424/777, 725; 514/456, 458, 725, 764, 886

(56) References Cited

U.S. PATENT DOCUMENTS

| 5,290,605 A | | 3/1994 | Shapira | |
| 5,648,377 A | * | 7/1997 | Bombardelli et al. | 514/456 |
| 5,725,844 A | * | 3/1998 | Gers-Barlag et al. | 424/59 |
| 5,895,652 A | | 4/1999 | Giampapa | |
| 5,925,348 A | * | 7/1999 | Riley et al. | 424/94.5 |
| 5,972,993 A | * | 10/1999 | Ptchelintsev | 514/449 |
| 6,110,478 A | * | 8/2000 | Harang | 414/401 |

FOREIGN PATENT DOCUMENTS

| EP | 0 659 402 A2 | | 6/1995 |
| JP | 11246396 | * | 9/1999 |
| WO | 9747278 | * | 12/1997 |
| WO | WO 97/47278 | | 12/1997 |
| WO | 9920242 | * | 4/1999 |

* cited by examiner

*Primary Examiner*—Jean C. Witz
(74) *Attorney, Agent, or Firm*—Burns, Doane, Swecker & Mathis, L.L.P.

(57) ABSTRACT

Lycopene and compositions comprised thereof, for example tomato plant extracts, are uniquely suited for treating, preventively and/or curatively, cutaneous signs of aging, in particular inhibiting damage to the skin and/or mucous membranes via inhibition of collagenases.

12 Claims, No Drawings

ADMINISTRATION OF LYCOPENE FOR COMBATING SKIN/MUCOUS MEMBRANE DAMAGE

CROSS-REFERENCE TO PRIORITY APPLICATIONS

This application claims priority under 35 U.S.C. §119 of FR-99/12507, filed Oct. 7, 1999, and FR-00/03849, hereby expressly incorporated by reference.

BACKGROUND OF THE INVENTION

1. Technical Field of the Invention

The present invention relates to the administration of lycopene or compositions comprised thereof, for treating, preventively and/or curatively, cutaneous signs of aging.

This invention especially relates to the administration of lycopene or compositions comprised thereof to inhibit damage to the skin and/or mucous membranes by the inhibition of collagenases. Too, this invention relates to a cosmetic regime/regimen for the skin and/or mucous membranes.

2. Description of the Prior Art

It is of course known that human skin is composed of two compartments or strata, namely, a surface compartment or layer, the epidermis, and a deep compartment or layer, the dermis.

The natural human epidermis is composed principally of three types of cells which are keratinocytes, melanocytes and Langerhans' cells, the vast majority being keratinocytes. Each of these cell types contributes by its specific functions to the essential role played by the skin in the body.

The dermis provides the epidermis with a solid support. It is also its source of nutrients. It is principally composed of fibroblasts and of an extracellular matrix, itself composed principally of collagen, of elastin and of a substance referred to as "ground" substance, which components are synthesized by the fibroblast. It also comprises leucocytes, mastocytes or tissue macrophages. It is also traversed by blood vessels and nerve fibers. In normal skin, namely, nonpathological and noncicatricial, the fibroblast is in the quiescent state, i.e., nonproliferative, not very active from a metabolic viewpoint and nonmobile.

It is the collagen fibers which provide the dermis with strength. The collagen fibers are composed of fibrils firmly attached to one another, thus forming more than ten types of different structures. The strength of the dermis is largely due to the entanglement of the collagen fibers, which are packed tight against one another in all directions. The collagen fibers contribute to the elasticity and to the tonicity of the skin and/or mucous membranes.

The collagen fibers are constantly replaced but this replacement decreases with age, which results in a thinning of the dermis. This thinning of the dermis is also due to pathological causes, such as, for example, the hypersecretion of corticoid hormones, certain pathologies or vitamin deficiencies (the case of vitamin C in scurvy). It is also accepted that extrinsic factors, such as ultraviolet radiation, tobacco or certain treatments (glucocorticoids, vitamin D and derivatives, for example), also have an effect on the skin and on its level of collagen.

However, various factors damage the collagen, with all the consequences which can be envisaged with regard to the structure and/or the firmness of the skin and/or mucous membranes.

Although highly resistant, collagen fibers are sensitive to certain enzymes known as collagenases. Damage to the collagen fibers results in the appearance of flabby and wrinkled skin which human subjects, preferring the appearance of a smooth and taut skin, have historically sought to combat.

Collagenases belong to a family of enzymes known as metalloproteinases (MMPs) which are themselves members of a family of proteolytic enzymes (endoproteases) which have a zinc atom coordinated to three (3) cysteine residues and a methionine in their active site and which decompose the macromolecular components of the extracellular matrix and of the basal laminae at neutral pH (collagen, elastin, and the like). Very widely distributed in the living world, these enzymes are present, but weakly expressed, in normal physiological situations, such as organ growth and tissue replacement.

Their overexpression in man and their activation are related, however, to numerous processes, sometimes pathological processes, which involve the destruction and the remodelling of the matrix. This results in either an uncontrolled resorption of the extracellular matrix or, conversely, in attaining a state of fibrosis.

The metalloproteinase family is composed of several well defined groups based on their similarities in terms of structure and of substrate specificity (see Woessner J.F., *Faseb Journal*, Vol. 5, 2145 (1991)). Among these groups, exemplary are collagenases intended to decompose fibrillar collagens (MMP-1 or interstitial collagenase, MMP-8 or neutrophil collagenase, or MMP-13 or collagenase 3), gelatinases which decompose collagen of type IV or any form of denatured collagen (MMP-2 or gelatinase A (72 kDa), or MMP-9 or gelatinase B (92 kDa)), stromelysins (MMP-3), the broad spectrum of activity of which is applicable to proteins of the extracellular matrix, such as glycoproteins (fibronectin, laminin), proteoglycans, and the like, or membrane metalloproteinases.

Prolonged exposure to ultraviolet radiation, particularly to type UV-A and/or UV-B ultraviolet radiation, has the effect of stimulating the expression of collagenases, particularly of MMP-1. This is one of the components of photoinduced cutaneous aging.

Furthermore, at menopause, the principal modifications relating to the dermis are a decrease in the level of collagen and in the dermal thickness. This results in thinning of the skin and/or of the mucous membranes in menopausal women. Women then experience a "dry skin" or tight skin feeling and a marked increase in surface fine wrinkles and fine lines is observed. The skin has a rough appearance on palpation. Finally, the skin exhibits reduced suppleness.

From the foregoing description of the importance of collagen in the structure of tissues, in particular of the skin and/or of the mucous membranes, need continues to exist in combating damage thereto in order to thus control aging, whether chronobiological or photoinduced aging, and the consequences thereof, such as the thinning of the dermis and/or the damage to collagen fibers which result in the appearance of flabby and wrinkled skin.

SUMMARY OF THE INVENTION

Accordingly, a major object of the present invention is the provision of unique treatment for exerting an inhibiting effect with regard to collagenases and which, to the extent possible, does not elicit any significant side effects.

Briefly, it has now surprisingly and unexpectedly been determined that lycopene exhibits an inhibitory activity with respect to the activity of collagenases.

DETAILED DESCRIPTION OF BEST MODE AND SPECIFIC/PREFERRED EMBODIMENTS OF THE INVENTION

More particularly according to the present invention, lycopene is a natural pigment which is present in ripe fruit, particularly in tomatoes. It belongs to the carotenoid family and its structure is similar to that of β-carotene.

The role of lycopene in the ripening of fruit is known to the prior art.

Lycopene is formulated into compositions with a tanning activity for its role with regard to the synthesis of melanin (WO-97/47278), in compositions suited for the treatment of the scalp and/or of acne, for its activity with regard to 5α-reductases (JP-2940964), or as an agent for combating free radicals (JP-A-8-283136).

To date, however, it is believed that the inhibitory activity of lycopene with regard to the activity of collagenases was unknown.

Thus, the present invention features the administration of lycopene or compositions comprised of lycopene, for treating, preventively and/or curatively, cutaneous signs of aging.

By the term "cutaneous signs of aging" is intended any modification in the external appearance of the skin due to aging, whether chronobiological and/or photoinduced, such as, for example, wrinkles and fine lines, withered skin, flabby skin, thinned skin, or lack of elasticity and/or of tone of the skin, but also any internal modification of the skin which is not reflected systematically by a modified external appearance, such as, for example, any internal damage to the skin, particularly to the collagen, resulting from exposure to ultraviolet radiation.

This invention thus also features the administration of lycopene or compositions comprised of lycopene for inhibiting the expression of the proteases of the extracellular matrix, particularly of metalloproteinases and even more particularly of type 1 metalloproteinase.

Too, the present invention features the administration of lycopene or compositions comprised of lycopene, for treating cutaneous conditions related to the menopause.

Also, this invention features the administration of lycopene or compositions comprised of lycopene, for combating skin wrinkles and fine lines.

The present invention also features the administration of lycopene or compositions comprised of lycopene, for combating withered skin.

And this invention as well features the administration of lycopene or compositions comprised of lycopene, for combating flabby skin.

Also as well, this invention features the administration of lycopene or compositions comprised thereof, for combating thinned skin.

And this invention also features the administration of lycopene or compositions comprised of lycopene, for combating lack of elasticity and/or of tone of the skin.

The lycopene according to the invention can be natural or synthetic in origin.

By the term "natural in origin" is intended any lycopene, in the pure state or in solution, whatever its concentration in said solution, obtained from a natural component, such as, for example, a plant extract, in particular a tomato.

By the term "synthetic in origin" is intended any lycopene, in the pure state or in solution, whatever its concentration in said solution, obtained by chemical synthesis.

When the lycopene is natural in origin, it can be obtained from plant material resulting from the whole plant cultivated in vivo or resulting from culturing in vitro.

By the term "cultivated in vivo" is intended any cultivation of conventional type, namely, in soil, in the open air or under glass, or soilless.

By the term "culturing in vitro" is intended any technique known to this art which makes it possible to artificially obtain a plant or a part of a plant. The selection pressure imposed by the physicochemical conditions during the growth of plant cells in vitro makes it possible to obtain a standardized plant material which is available throughout the year, in contrast to plants cultivated in vivo.

Preferably, according to the invention, a plant resulting from cultivation in vivo is employed. Very preferably, a lycopene-rich tomato extract is utilized.

Any extraction method known to this art can be used to prepare the lycopene according to the invention.

The lycopene can be in aqueous suspension or in alcoholic solution, in particular in ethanolic solution.

By the term "aqueous suspension" is intended a solution composed entirely or partially of water. Exemplary are water itself, aqueous/alcoholic solutions in any proportion or solutions composed of water and of a compound such as propylene glycol in any proportion.

An exemplary lycopene-rich tomato extract well suited for administration according to the invention is that marketed by the company Metaphar under the trademark LycOMato®, comprised of an oleoresin extract containing 6% of pure lycopene.

The extract can constitute, by itself alone, the active principle of the compositions of the invention.

The amount of extract which can be used according to the invention is, of course, a function of the effect desired and can thus vary over wide limits.

To provide an order of magnitude, the lycopene can be administered in the pure state in an amount constituting from $10^{-12}$% to 20% of the total weight of the composition and preferably in an amount constituting from $10^{-8}$% to 10% of the total weight of the composition.

Indeed, one skilled in this art, when employing lycopene in the form of a solution, for example a plant extract, is cognizant of how to adjust the amount of solution included in the final composition to provide an amount of lycopene in agreement with those useful amounts described.

The compositions of the invention can be formulated in any form whatsoever suited equally well for topical application onto the skin and/or mucous membranes and/or hair and for oral administration.

Preferably, the compositions of the invention are formulated for oral administration.

The compositions of the invention are characteristically cosmetic or dermatological compositions. Preferably, the subject compositions are cosmetic compositions. These compositions are cosmetic compositions as same are suited to improve the general skin appearance of the individual user.

Very preferably, the compositions of the invention are cosmetic compositions formulated for oral administration.

For oral administration, the compositions of the invention can be provided in any suitable form, particularly in the form of a solution to be taken orally, of a tablet, of a capsule, including a hard gelatin capsule, of a nutritional food or of a nutritional supplement.

Such compositions additionally comprise at least one appropriate excipient suited for oral administration.

For administration by topical application onto the skin, hair and/or mucous membranes, the compositions according to the invention very obviously comprises a cosmetically acceptable vehicle, diluent or carrier, i.e., a vehicle compatible with the skin, mucous membranes, nails or hair, and can be provided in any preparation form normally employed for topical application, in particular in the form of an aqueous, aqueous/alcoholic or oily solution, of an oil-in-water or water-in-oil or multiple emulsion, of an aqueous or oily gel, of a liquid, pasty or solid anhydrous product or of a dispersion of oil in aqueous phase comprising spherules, it being possible for these spherules to be polymeric nanoparticles, such as nanospheres and nanocapsules, or more particularly lipid vesicles of ionic and/or nonionic type.

Such compositions can be more or less fluid and can have the appearance of a white or colored cream, of an ointment, of a milk, of a lotion, of a serum, of a paste or of a foam. Same can optionally be applied to the skin in aerosol form. Same can also be provided in solid form, for example in stick form. These can be useful care products, such as cleansing products, makeup products or simple deodorant products.

In known fashion, the compositions of the invention can contain adjuvants and additives conventional in the cosmetics and dermatological fields, such as hydrophilic or lipophilic gelling agents, hydrophilic or lipophilic active principles, preservatives, antioxidants, solvents, fragrances, fillers, screening agents, pigments and colorants, chelating agents, odor absorbers and dyes. The amounts of these various adjuvants and additives are those conventional in the fields under consideration, for example from 0.01% to 20% of the total weight of the composition. These adjuvants and additives, according to their nature, can be formulated into the fatty phase, into the aqueous phase, into the lipid vesicles and/or into the nanoparticles.

When the compositions of the invention are emulsions, the proportion of the fatty phase advantageously ranges from 5% to 80% by weight and preferably from 5% to 50% of the total weight of the composition. The oils, the emulsifiers and the coemulsifiers included in the composition in emulsion form are selected from among those conventional in the field under consideration. The emulsifier and the coemulsifier are advantageously present in the composition in a proportion ranging from 0.3% to 30% by weight and preferably from 0.5% to 20% of the total weight of the composition.

Exemplary oils according to the invention include mineral oils, oils of plant origin (apricot oil, sunflower oil), oils of animal origin, synthetic oils, silicone oils and fluorinated oils (perfluoropolyethers). Exemplary fatty substances include the fatty alcohols (cetyl alcohol), fatty acids or waxes (beeswax).

Exemplary emulsifiers and coemulsifiers according to the invention include the fatty acid esters of polyethylene glycol, such as PEG-40 stearate or PEG-100 stearate, or polyol fatty acid esters, such as glyceryl stearate and sorbitan tristearate.

And exemplary hydrophilic gelling agents include the carboxyvinyl polymers (carbomer), acrylic copolymers, such as acrylate/alkyl acrylate copolymers, polyacrylamides, polysaccharides, natural gums and clays and exemplary lipophilic gelling agents include the modified clays, such as bentones, metal salts of fatty acids, hydrophobic silica and polyethylenes.

The present invention also features a method or regime/regimen for the cosmetic treatment of the skin to stimulate the synthesis of collagen and/or to combat cutaneous conditions related to age and/or to the menopause and/or to combat thinning of the dermis and/or to combat the appearance of flabby and/or wrinkled skin, comprising topically applying a cosmetic composition containing at least lycopene onto the skin, the hair and/or the mucous membranes, or ingesting same.

The cosmetic treatment of the invention can be conducted by administering the cosmetic compositions as described above according to the usual operating techniques for such compositions. For example: application of creams, of gels, of serums, of lotions, of ointments, of milks, of mousses, of shampoos, or of antisun compositions onto the skin or to hair, or application of dentifrice to the gums and preferably by oral administration of a solution to be taken orally, of a syrup, of a tablet, of a capsule, including a hard gelatin capsule, of a nutritional food or of a nutritional supplement.

In order to further illustrate the present invention and the advantages thereof, the following specific examples are given, it being understood that same are intended only as illustrative and in nowise limitative.

In said examples to follow, all parts are percentages are given by weight, unless otherwise indicated.

EXAMPLE 1

Evaluation of the Activity of Lycopene With Respect to Interstitial Collagenases The activity of a lycopene-rich tomato extract (LycOMato® marketed by Metaphar) was studied on HeLa cells transfected with an expression vector encoding a portion of the promoter of collagenase cloned upstream of the gene for chloramphenicol acetyltransferase (CAT).

The study made it possible to evaluate the effectiveness of a product in inhibiting the induction of the transcription of the gene for collagenase by phorbol 12-myristate 13-acetate (PMA).

The test was carried out on HeLa cells (ATCC CCL2), into which had been introduced the promoter of the gene for collagenase 1 (3.8 kB) cloned upstream of the gene for chloramphenicol acetyltransferase (CAT).

The cells were exposed to PMA at a concentration of 10 nM for 24 hours.

Before administration of PMA, the cells were contacted for 2 hours with lycopene (LycOMato® marketed by Metaphar) at concentrations varying from $10^{-7}\%$ to $10^{-4}\%$, representing lycopene concentrations ranging from $6\times10^{-9}\%$ to $6\times10^{-6}\%$.

Assaying of the CAT was carried out using a "CAT-Elisa" kit marketed by Boehringer, according to the supplier's instructions.

A "base level" for the expression of the CAT was measured in cells which had neither received PMA nor were treated with the test product.

The results of the test, reported in the following Table, are expressed with respect to the base level (100%) as percentage of inhibition of the expression of the CAT gene.

These results thus reflect the activity of the promoter of collagenase 1 after induction by PMA and in the presence or absence of the test product.

TABLE

| LycOMato ® (as %) | 0 | $10^{-7}$ | $10^{-6}$ | $10^{-5}$ | $10^{-4}$ |
|---|---|---|---|---|---|
| % of inhibition of the activity of the promoter | 0 | 15 | 25 | 40 | 50 |

These results clearly evidence the inhibitory effect of lycopene on the synthesis of collagenase 1 by inhibition of the activity of its promoter.

EXAMPLE 2

The following are specific examples of formulations according to the invention.

These compositions were formulated by simple intimate admixing of the various components thereof.

| Composition 1 - Soft capsules: | |
|---|---|
| Excipients: | |
| Soybean oil | 40 mg |
| Wheat germ oil | 85 mg |
| Soya lecithins | 25 mg |
| Vitamin: | |
| Natural tocopherols | 3 mg |
| Components: | |
| Lycopene 6% | 175 mg |

| Composition 2 - Shampoo: | |
|---|---|
| Lycopene | $10^{-7}$% |
| Hydroxypropylcellulose (Klucel H ®, marketed by Hercules) | 1.00% |
| Fragrance | 0.50% |
| Preservative | 0.30% |
| Water | q.s. for $10^{-7}$% |

| Composition 3 - Facial care cream (oil-in-water emulsion): | |
|---|---|
| Lycopene | 0.01% |
| Glyceryl stearate | 2.00% |
| Polysorbate 60 (Tween 60 ®, marketed by ICI) | 1.00% |
| Stearic acid | 1.40% |
| Triethanolamine | 0.70% |
| Carbomer | 0.40% |
| Liquid fraction of karite butter | 12.00% |
| Perhydrosqualene | 12.00% |
| Antioxidant | 0.05% |
| Fragrance | 0.50% |
| Preservative | 0.30% |
| Water | q.s. for 100.00% |

| Composition 4 - Gel for the skin: | |
|---|---|
| Lycopene | 0.01% |
| All-trans-retinoic acid | 0.05% |
| Hydroxypropylcellulose (Klucel H ®, marketed by Hercules) | 1.00% |
| Antioxidant | 0.05% |
| Isopropanol | 40.00% |
| Preservative | 0.30% |
| Water | q.s. for 100.00% |

| Composition 5 - Gel for face care: | |
|---|---|
| Lycopene | $10^{-5}$% |
| Hydroxypropylcellulose (Klucel H ®, marketed by Hercules) | 1.00% |
| Antioxidant | 0.05% |
| Isopropanol | 40.00% |
| Preservative | 0.30% |
| Water | q.s. for 100.00% |

| Composition 6 - Gel: | |
|---|---|
| Lycopene | 0.10% |
| Hydroxypropylcellulose (Klucel H ®, marketed by Hercules) | 1.00% |
| Antioxidant | 0.50% |
| Lidocaine hydrochloride | 2.00% |
| Isopropanol | 10.00$ |
| Preservative | 0.30% |
| Water | q.s. for 100.00% |

| Composition 7 - Sunburn care cream (oil-in-water emulsion): | |
|---|---|
| Lycopene | $10^{-6}$% |
| Glyceryl stearate | 2.00% |
| Polysorbate 60 (Tween 60 ®, marketed by ICI) | 1.00% |
| Stearic acid | 1.40% |
| Glycyrrhetinic acid | 2.00% |
| Triethanolamine | 0.70% |
| Carbomer | 0.40% |
| Liquid fraction of karite butter | 12.00% |
| Sunflower oil | 10.00% |
| Antioxidant | 0.05% |
| Fragrance | 0.50% |
| Preservative | 0.30% |
| Water | q.s. for 100.00% |

| Composition 8 Antiwrinkle care cream for the face (oil/water emulsion): | |
|---|---|
| Lycopene | $10^{-7}$% |
| Glyceryl stearate | 2.00% |
| Polysorbate 60 (Tween 60 ®, marketed by ICI) | 1.00% |
| Stearic acid | 1.40% |
| 5-(n-Octanoyl)salicylic acid | 0.50% |
| Triethanolamine | 0.70% |
| Carbomer | 0.40% |
| Liquid fraction of karite butter | 12.00% |
| Perhydrosqualene | 12.00% |
| Antioxidant | 0.05% |
| Fragrance | 0.50% |
| Preservative | 0.30% |
| Water | q.s. for 100.00% |

| Composition 9 - Lotion: | |
|---|---|
| Lycopene | 1.00% |
| Glycolic acid | 50.00% |
| Hydroxypropylcellulose (Klucel ®, marketed by Hercules) | 0.05% |
| Preservative | 0.30% |
| NaOH | q.s. for pH = 2.8 |
| Ethanol | q.s. for 100.00% |

| Composition 10 - Makeup-removing lotion for the face: | |
|---|---|
| Lycopene | $10^{-4}$% |
| Antioxidant | 0.05% |
| Isopropanol | 10.00% |
| Preservative | 0.30% |
| Water | q.s. for 100.00% |

While the invention has been described in terms of various specific and preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A method for treating an individual having cutaneous signs of aging caused by expression of proteases in the extracellular matrix comprising administering to said individual an amount of lycopene effective to substantially inhibit the expression of said proteases in the extracellular matrix of said individual.

2. The method as defined by claim 1, said lycopene being natural in origin.

3. The method as defined by claim 1, said lycopene being synthetic in origin.

4. The method as defined by claim 1, comprising administering pure lycopene or solution thereof.

5. The method as defined by claim 1, comprising administering a lycopene-containing plant extract.

6. The method as defined by claim 5, comprising administering a lycopene-containing tomato plant extract.

7. The method as defined by claim 6, comprising administering an oleoresin tomato plant extract containing 6% of lycopene.

8. The method as defined by claim 1, comprising administering a composition containing from $10^{-12}$% to 20% by weight of lycopene.

9. The method as defined by claim 8, comprising administering a composition containing from $10^{-8}$% to 10% by weight of lycopene.

10. The method as defined by claim 8, said composition being formulated for topical application onto the skin, hair and/or mucous membranes.

11. The method as defined by claim 8, said composition being formulated for oral ingestion.

12. The method as defined by claim 11, said composition comprising a syrup, tablet, capsule, or nutritional food or supplement.

\* \* \* \* \*